United States Patent
Hartel et al.

[11] Patent Number: 5,159,898
[45] Date of Patent: Nov. 3, 1992

[54] PROCESS AND APPARATUS FOR UTILIZATION OF FUELS WITH ALCOHOL ADDITIVES FOR AN INTERNAL COMBUSTION ENGINE

[75] Inventors: Gunter Hartel, Neuss; Armin Schurfeld, Meerbush; Karl-Henrich Losing, Alpen; Dieter Thonnessen, Viersen; Ulrich Remde, Meerbush, all of Fed. Rep. of Germany

[73] Assignee: Pierburg GmbH, Neuss, Fed. Rep. of Germany

[21] Appl. No.: 771,367

[22] Filed: Oct. 1, 1991

[30] Foreign Application Priority Data

Oct. 1, 1990 [DE] Fed. Rep. of Germany ....... 4031009

[51] Int. Cl.$^5$ .............................................. F02B 75/12
[52] U.S. Cl. ..................................... 123/1 A; 123/494; 73/61.77; 73/64.54
[58] Field of Search ................. 123/1 A, 494; 73/61.3

[56] References Cited

U.S. PATENT DOCUMENTS

| | | | |
|---|---|---|---|
| 3,528,439 | 9/1970 | Plucker, III | 73/61.3 |
| 3,528,440 | 9/1970 | Plucker, III | 73/61.3 |
| 4,589,277 | 5/1986 | Collins et al. | 73/61.3 |
| 4,905,655 | 3/1990 | Maekawa | 123/1 A |
| 4,962,746 | 10/1990 | Miyata et al. | 123/1 A |
| 4,974,552 | 12/1990 | Sickafus | 123/494 |
| 4,984,452 | 1/1991 | Howard et al. | 73/61.3 |
| 4,989,570 | 2/1991 | Kuribara | 123/494 |
| 5,044,344 | 9/1991 | Tuckey et al. | 123/494 |
| 5,060,619 | 10/1991 | Sakurai | 123/1 A |

FOREIGN PATENT DOCUMENTS

| | | |
|---|---|---|
| 2259323 | 6/1974 | Fed. Rep. of Germany . |
| 3841471 | 6/1990 | Fed. Rep. of Germany ..... 123/1 A |
| 0218741 | 9/1986 | Japan ................... 123/1 A |

*Primary Examiner*—E. Rollins Cross
*Assistant Examiner*—Erick Solis
*Attorney, Agent, or Firm*—Ladas & Parry

[57] ABSTRACT

A process and apparatus for utilization of fuels with alcohol additives for an internal combustion engine which are characterized by the fact that at the present time comercial types of fuel have approximately the same molecular weights, which are clearly distinct from the molecular weights of methanol and ethanol. By complete vaporization of a sample volume of fuel, depending on the admixture of alcohol to standard fuel, different volumes of vaporized fuel samples are produced, or different pressures are obtained if the volume is constant. Based thereon and on the sample temperature a correction signal is formed which is characterized by the alcohol and its content in the sample (as compared with reference values stored in a control device), and the correction signal can be utilized to regulate the engine control variables.

16 Claims, 2 Drawing Sheets

PROCESS AND APPARATUS FOR UTILIZATION OF FUELS WITH ALCOHOL ADDITIVES FOR AN INTERNAL COMBUSTION ENGINE

FIELD OF THE INVENTION

The invention relates to a process and apparatus for the utilization of fuels with alcohol additives for an internal combustion engine.

BACKGROUND

In addition to high test and regular gasoline and diesel fuel, alcohols, such as methanol, ethanol, propanol, isobutanol, etc. are suitable as fuels for internal combustion engines.

The calorific value of the combustible fuel-air mixture is a determining factor for the power of the engine. For a stoichiometric mixing ratio, the calorific value of the mixture for substantially all utilizable liquid fuels and liquified petroleum gases lies between 700 and 735 Kcal/kg; they are thus almost equal and engine power losses should not be expected by mixing methanol or other alcohols into the fuel mixture. In addition, most of the other properties of alcohols are such that they can be mixed with common liquid fuels without anything further and they cause no disturbances in practical engine operation.

An alcohol composition is particularly desirable for the reason that alcohols are suitable as a refining fuel for low-grade gasolines. By adding, for example, methanol to regular gasoline, the anti-knock property of the gasoline can be substantially improved, so that with this mixture even high compression internal combustion engines can be operated. Therefore, it becomes unnecessary to add anti-knocking agents to the fuel, which may be harmful to the environment.

Therefore, alcohols are becoming of increasing importance in the USA for environmental reasons, particularly due to the stricter regulations in California.

In addition, alcohols, particularly methanol, can be produced from coal relatively cheaply, and alcohols will thus be available in large quantities well into the distant future. In particular, ethanol is environmental-friendly, if it is obtained from plant products. Alcohols are thus a suitable supplement for fossil fuels whose supply is ultimately limited.

However, it is disadvantageous that the specific minimum air requirement for complete combustion in the case of alcohols is less than for conventional fuels. For the same aspirated air quantity, a correspondingly higher quantity of fuel must be introduced to the engine in the case of alcohol or for a mixture of gasoline and alcohol in order to obtain a stoichiometric air-fuel ratio. This makes necessary a corresponding adjustment of the mixture-forming means, i.e. fuel injection or carburation systems of the internal combustion engine. Moreover, since the alcohols are usually added in varying amounts, as necessary, or can vary in the vehicle fuel tank when different types of fuel are added to the tank, the required air-fuel ratio for a stoichiometric mixture must be determined anew in the electronic control device for the mixture-forming means according to the alcohol fraction in the fuel tank.

In DE-OS 40 19 188 there is disclosed a multicomponent engine control with a fuel sensor for determining the mixture fraction of methanol in a fuel-methanol mixture, whose output signal is used for subsequently establishing a stored engine fuel-control dielectric sensor, which contains two electrode plates immersed in the fuel and arranged in spaced relation from one another. The dielectric constant of the fuel is detected by measurement of the capacitance between the two electrode plates, the added fraction of methanol being derived from the dielectric constant.

This measurement system, however, has a high sensitivity to vapor lock. In addition, this fuel sensor is only suitable to detect the mixture fraction of a previously known alcohol (e.g., methanol).

A device for automatic adaptation of an internal combustion engine to the requirements of the selective use of various types of liquid fuels is known from DE-OS 22 59 323 which has a closed measurement tank for flow therethrough of fuel from an inlet to an outlet. In the measurement tank a partial quantity of fuel is vaporized under the effect of applied heat, whereby the relative size of the vapor-filled space inside the measurement tank serves as a measurement for determining the different types of fuels.

A disadvantage of this system is that it can only be established whether a specific fraction has been exceeded or fallen below, whereby even here this fraction must be known beforehand in order to arrange the measurement sensor of this device at a specific level in the measurement tank.

SUMMARY OF THE INVENTION

The invention is based on the fact that at the present time commercial types of fuel all have approximately the same molecular weight, which, however, is clearly different from the molecular weights of alcohol additives, such as methanol and ethanol. Thus, one mole of commercial fuel weighs about 98 grams, while one mole of ethanol is approximately 46 grams, and one mole of methanol, approximately 32 grams.

Different volumes of vaporized fuel samples are are produced upon the complete vaporization of a specific sample volume, depending on the proportion of alcohol addition to the standard fuel. Different pressures result, depending on the alcohol addition, when the volume is fixed. For a precise evaluation of the alcohol fraction, it is necessary each time to determine the sample temperature and to take into consideration its effect on the parameter to be measured.

A correction signal is formed from these values (volume and/or pressure and/or temperature change) after vaporizing the sample quantity of fuel by comparison with reference values stored in a control device. The control of the engine can be varied by the correction signal.

In order to carry out the process, the invention contemplates apparatus in which a sample quantity of fuel is completely vaporized and the pressure, volume, and temperature changes are measured to determine the particular alcohol present in the fuel mixture and its concentration.

By means of this invention, it is possible to determine the presence of particular alcohols and their percentages in the fuel mixture, and for example, a sample is vaporized after each startup of the engine, and the engine is operated accordingly.

The apparatus and the method of the invention have the advantage that they are substantially insensitive to variation in the composition of the fuel as for example, for winter and summer operation.

Additionally, the method and apparatus are insensitive to vapor lock.

Figure 1:
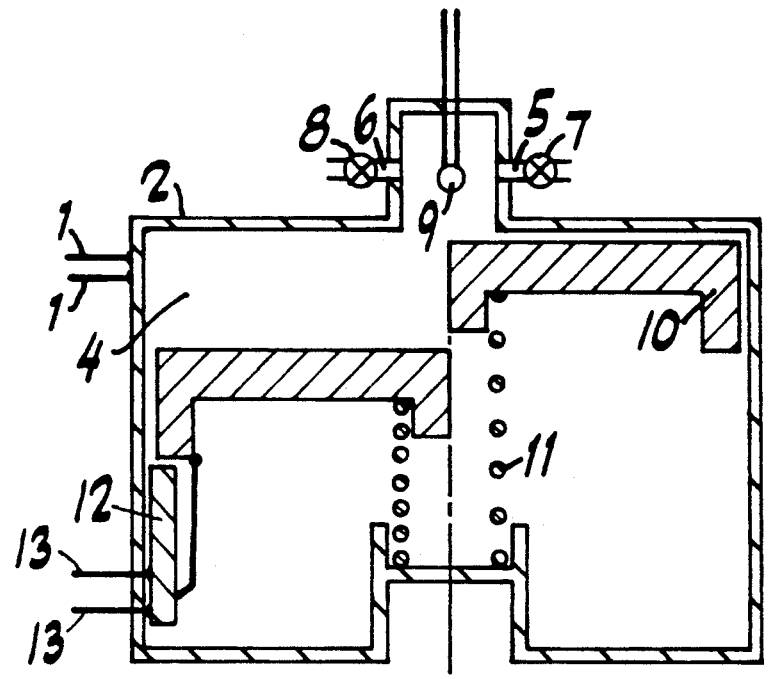
FIG. 1 is a sectional view through a device for vaporizing a sample quantity of fuel according to one embodiment of the invention.
Figure 2:
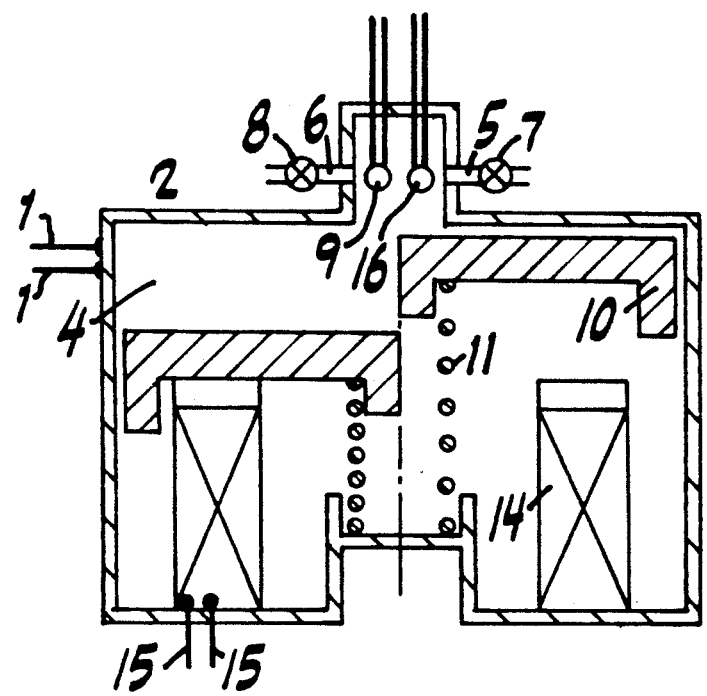
FIG. 2 is a sectional view through another embodiment of a device for vaporizing a sample quantity of fuel.
Figure 3:
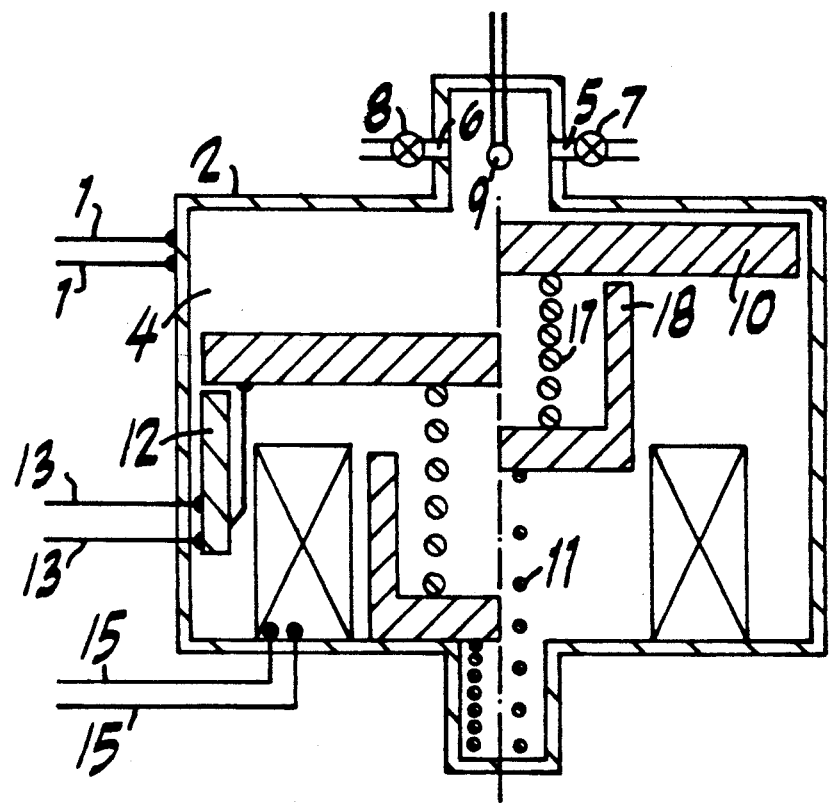
FIG. 3 is a sectional through another embodiment of a device for vaporizing a sample quantity of fuel.

The right side of the sectional views in FIGS. 1-3 shows the device in the initial or rest position, while the left side shows the device in a measurement state.

DETAILED DESCRIPTION OF PREFERRED EMBODIMENTS

FIG. 1 shows a device for vaporizing a sample quantity of fuel comprising a housing 2, which can be heated by connecting a voltage supply (not shown) to electrical connections 1. The housing enclosed a sampling chamber 3 which opens into a vaporization chamber 4. The sampling chamber 3 has inlet and outlet channels 5, 6, which are opened and closed by respective valves 7, 8. A temperature sensor is disposed in the sampling chamber 3. A pistin 10 is mounted in vaporization chamber 4 for axial displacement against the force of a spring 11. The position of the piston is determined by a sensor 12, which can be in the form of a potentiometer or optical sensor. The sensor 12 is connected to a control device (not shown) by means of electrical leads 13.

In the rest position, fuel flows continuously through valve 7 and inlet channel 5 into sample chamber 3 and exits from the sampling chamber via outlet channel 6 and vale 8, whereby fresh fuel is continuously available for measurement. Piston 10 is urged upwardly against the housing by the force of spring 11 and seals the sampling chamber 3.

When a measurement operation is to take place, the inlet channel 5 is closed by valve 7 and outlet channel 6 is closed by valve 8. A sample quantity of fuel is then in the housing and after conditioning to a constant temperature (e.g. 30° C.) and a predetermined pressure Po, the sample is heated in a first process step to a predetermined temperature (e.g. 220° C.), until the sample quantity of fuel is vaporized. In a second process step, the change in volume arising due to vaporization, which is represented by the displaced position of piston 10, is measured by the sensor 12. This value is compared in a third process step with a reference value for standard fuel stored in the control device, taking into consideration the temperature, and a correction signal is produced based on the difference therebetween. The correction signal is utilized to regulate engine control variables, such as the amount of fuel or air supplied to the engine to adjust the air-fuel ratio in a fourth process steps.

The correction signal is stored in a fifth process step until it is confirmed or modified by a new fuel sample measurement.

Thus, if the measurement operation of the device is terminated so that the heating of the fuel sample is discontinued and outlet channel 6 is opened in a sixth process step, the volume of chamber 4 is reduced, and piston 10 is urged to the top of the housing. Inlet channel 5 is opened and the sampling chamber is flushed and cooled with fresh fuel mixture.

In another embodiment of the vaporizing device as shown in FIG. 2, a solenoid 14 is arranged in vaporization chamber 4, which can be controlled by electrical connections 15 by means of the control device (not shown). In addition to temperature sensor 9, sample chamber 3 has a pressure sensor 16.

In this embodiment, in a first process step, after conditioning of the sample quantity of fuel and closing valve 8, a predetermined volume is established by actuation solenoid 14, causing piston 10 to be lowered until a specific volume is reached. Piston 10 can also be displaced by suction means.

Then, the sample quantity of fuel is vaporized at a constant temperature (e.g. 120° C.). The vaporization produces a pressure change, whose magnitude is determined in a second process step by pressure sensor 16. This pressure value is compared in a third process step with reference values for standard fuel stored in the control device, taking into consideration the two constants (temperature and volume), and a correction signal is produced based on the difference between the pressure values.

The fifth and sixth process steps are similar to that already described for the process with the device of FIG. 1. After formation and storage of the correction value, the heating is discontinued, the current feed to solenoid 14 is terminated, outlet channel 6 is opened by valve 8, and the gas is compressed and recondensed to liquid.

After opening inlet channel 5 by valve 7, fresh fuel is supplied for flushing and cooling sampling chamber 3, and the device is ready for a new measurement operation.

Another embodiment is shown in FIG. 3 which has in vaporization chamber 4 a second piston 18 formed as an armature and coupled to piston 10 by means of a tension spring 17, which is expanded and contracted opposite spring 11. The other structural parts of this device are the same as in FIG. 1 and 2 and their description is omitted.

In this embodiment, after conditioning the sample quantity of fuel and closing the sampling chamber 3 in the first process step, an increased volume for the sample is established until a predetermined pressure has been reached for said volume. This is effected by actuating solenoid 14 and pulling armature 18 to a stop at the bottom of the vaporization chamber 4. Piston 10 is displaced to a position dependent on the composition and temperature of the sample quantity of fuel by means of tension spring 17, and this position is detected by potentiometer 12.

During the heating and vaporization of the sample quantity of fuel at a constant temperature, for example, 220° C., the piston travels further in the direction of armature 18 due to the equilibration of the increase in pressure, and assumes a position dependent on the fraction of alcohol in the fuel mixture.

This position is measured according to process step 2 by sensor 12 (which may also be formed as a contact-free sensor), and serves as the base value for formation of the correction signal according to process step 3. Process steps 4-6 which follow take place as already described.

An embodiment analogous to that of FIG. 3 employs a final position switch for detecting the position of piston 10. In this embodiment, piston 10 is first brought to a defined position (given volume of chamber 4) by means of solenoid 14 and tension spring 17, and then the temperature is regulated (e./g. greater than 220° C.) until piston 10 reaches the final position switch. Pressure and volume are thus constant, while the temperature value is utilized to form the correction signal according to the above-described process.

For the latter two variants, the use of an expensive pressure sensor is not necessary.

The correction signal formed on the basis of the pressure and/or volume and/or temperature change in the third process step and stored in the fifth process step according to the individual embodiments, may also be used during a restarting of the internal combustion engine until it is confirmed or replaced according to a new fuel sample measurement.

Increasingly stricter exhaust regulations make it necessary that even small operating periods of the internal combustion engine (for example, cold starting, idling, hot starting and the like) must be subjected to an ever increasing optimization of exhaust emissions. For this reason, the previously described process is further improved as follows.

During starting (cold or hot start) of the internal combustion engine, a measurement cycle is immediately initiated to form the correction signal; however, the new correction signal is present only after a specific time, which is necessary in order to run through process steps 1 to 6.

For starting and until establishing a current correction signal, the last stored correction signal is used.

After starting, generally several measurements will be conducted in sequence until the measurement value has stabilized.

Thus, after stopping for filling the fuel tank, the mixture of fuel instantaneously introduced into the injection valves is sampled, if the measurement device is arranged in the return line to the tank which is preferable.

However, it is also conceivable to correct the last stored correction signal as a function of the filling state of the fuel tank or to override it until a new correction signal is given by the vaporization device.

In this way, in addition to the stored correction signal, the filling state of the fuel tank is detected when the internal combustion engine is turned off and is also stored, and compared with the actual filling state upon starting again. It must still be distinguished how quickly the actual filling state is detected. If an actual filling state is present only after the presence of the new correction signal (slow tank indicated), the following process course A is provided, while for a rapid tank indication, thus in the presence of the actual filling state before establishing the new correction signal, process course B is provided.

Process course A (slow tank indication)

Starting is produced with the use of the last stored correction signal, while at the same time the tank filling state stored upon turning off the internal combustion engine is evaluated, i.e., it is established whether the fuel tank was, for example, more than half full or less than half full. If it is established that it is more than half full, then the stored correction signal is used until the correction signal is established, since it is assumed that the tank filling has not occurred after turning off the internal combustion engine, or if, in fact, the fuel tank was filled, a falsification due to the added fuel is not a problem. If it is established that the fuel tank is less than half full, it is assumed that a fill-up has occurred and the last stored correction signal is correction to an average correction, signal (for example, with that of a standard fuel) according to a predetermined function (linear, exponential function, stepped function, etc.). After establishing a new correction signal from the vaporization device, further operation is immediately corrected to this new correction signal.

Process course B (rapid tank indication)

With the establishment of no change in the tank filling state, until the new correction signal is used. established, the stored correction signal is used If a change in the tank filling state has occurred, process B continues as process A when it has been established that the tank is less than half full.

In the case of operation of a $\lambda=1$ control, operation is conducted with a stoichiometric mixture. In this phase of operation it is possible to quantitively check the correction signal and to adaptively correct it in the case of a deviation.

What is claimed is:

1. A process for determining the presence of an alcohol additive in a fuel mixture for an internal combustion engine and for correcting engine operation based thereon, said process comprising;
   in a first process step, heating a sample quantity of fuel to vaporize said sample quantity;
   in a second process step, measuring properties of the vaporized sample quantity;
   in a third process step, determining from the measured properties of the vaporized sample quantity the presence of alcohol in said sample quantity and its concentration based on the difference between the molecular weight of fuel along without alcohol and the molecular weight of alcohol, and producing a correction signal based on said difference; and
   in a fourth process step controlling variables affecting engine operation on the basis of said correction signal.

2. A process as claimed in claim 1 wherein:
   in said first process step, the sample quantity of fuel is maintained at a predetermined volume;
   in the second process step, pressure and temperature changes due to the vaporization of the sample are measured by respective sensors; and
   in said third process step, said pressure and temperature changes are respectively compared with reference values for said fuel along to form said correction signal.

3. A process as claimed in claim 1 wherein:
   in said first process step, the sample quantity of fuel is maintained at a predetermined pressure as the sample quantity of fuel is heated until said sample quantity is vaporized;
   in said second process step, volume and temperature changes due to the vaporization of the sample are measured by respective sensors, and
   in said third process step, said volume and temperature changes are respectively compared with reference values for standard fuel to form said correction signal.

4. A process as claimed in claim 1 wherein:
   in said first process step, the sample quantity of fuel is maintained at a predetermined volume after which the sample quantity of fuel is heated to a predetermined temperature at which a prespecified volume is reached, and thereafter, the temperature is increased until the sample quantity of fuel is vaporized;

in said second process step, the temperature reached after vaporization is measured by a sensor; and in said third process step, the temperature is compared to a reference value for standard fuel to form said correction signal from the difference.

5. A process as claimed in claim 1 further comprising in a sixth process step, halting heating of the fuel sample, reducing the volume of fuel sample, and flushing the fuel sample and replacing it with a fresh fuel sample.

6. A process as claimed in claim 1 comprising in a fifth process step, storing said correction signal for continued use until replaced.

7. A process as claimed in claim 6 comprising utilizing said stored correction signal for control of engine operation when starting the engine.

8. Apparatus for vaporizing a sample quantity of fuel for controlling an internal combustion engine, said apparatus comprising:

a sampling chamber for a sample quantity of fuel;

a vaporization chamber communicating with said sampling chamber;

means for heating said sampling chamber to vaporize the sample quantity of fuel therein and cause the vaporized fuel to expand into said vaporization chamber;

a piston subject to the pressure of the vaporized fuel in said vaporization chamber;

spring means acting on said piston in opposition to the pressure of said vaporized fuel; and sensor means for measuring properties of the vaporized sample quantity which are indicative of alcohol in the sample quantity of fuel based on the difference between molecular weights of fuel along without alcohol and molecular weight of alcohol.

9. Apparatus as claimed in claim 8 comprising a fuel inlet channel and a fuel outlet channel for said sampling chamber and valve means in said channels for opening and closing the same.

10. Apparatus as claimed in claim 8 wherein said sensor means comprises a position sensor in said vaporization chamber for detecting the position of said piston.

11. Apparatus as claimed in claim 10 comprising means connected to said piston to displace the piston to a determined location.

12. Apparatus as claimed in claim 11 wherein said means to displace the piston comprises electromagnetic means.

13. Apparatus as claimed in claim 11 wherein said means to displace the piston comprises an armature, a tension spring connecting said piston and said armature, and electromagnetic means acting on said armature.

14. Apparatus as claimed in claim 13 wherein said sensor comprises a terminal position switch.

15. Apparatus as claimed in claim 8 wherein said sensor means comprises a temperature sensor in said sampling chamber.

16. Apparatus as claimed in claim 8 wherein said sensor means comprises a pressure sensor in said sampling chamber.

* * * * *